US00PP11247P

United States Patent [19]

Segers

[11] Patent Number: Plant 11,247

[45] Date of Patent: Feb. 29, 2000

[54] HYBRID TEA ROSE PLANT NAMED 'PRESUR'

[75] Inventor: Theodorus A. Segers, Hoofddorp, Netherlands

[73] Assignee: Prego Royalty B.V., Naaldwijk, Netherlands

[21] Appl. No.: 08/929,644

[22] Filed: Sep. 15, 1997

[51] Int. Cl.[7] ..... A01H 5/00

[52] U.S. Cl. ..... Plt./135

[58] Field of Search ..... Plt./11, 16, 17, Plt./15, 130, 135, 134, 146

*Primary Examiner*—Howard J. Locker
*Attorney, Agent, or Firm*—C. A. Whealy

[57] ABSTRACT

A distinct cultivar of hybrid tea rose plant named 'Presur', characterized by its large soft orange flowers; pleasant fragrance; freely branching plant habit with numerous flowering stems per plant; long stem length; and excellent postproduction longevity.

1 Drawing Sheet

The present invention relates to a new and distinct cultivar of hybrid tea rose plant, botanically known as *Rosa hybrida,* commercially used as a cut flower, and hereinafter referred to by the cultivar name 'Presur'.

The new cultivar is a product of a planned breeding program conducted by the inventor in Rijsenhout, The Netherlands. The objective of the breeding program was to develop cut rose varieties with novel and attractive flower colors, numerous flowering stems per plant, and fragrance. The new cultivar originated from a cross made by the inventor in 1989 of two proprietary seedlings. The proprietary selection P24 was the female, or seed, parent, and the proprietary selection P7 was male, or pollen, parent. The cultivar Presur was discovered and selected by the inventor as a flowering plant within the progeny of the stated cross in a controlled environment in Rijsenhout, The Netherlands.

Asexual propagation of the new cultivar by cuttings taken at Rijsenhout, The Netherlands, has shown that the unique features of this new rose plant are stable and reproduced true to type in successive generations.

The following traits have been repeatedly observed and are determined to be the unique characteristics of 'Presur'. These characteristics in combination distinguish the new rose plant as a new and distinct cultivar:

1. Large soft orange flowers that are golden yellow before opening.
2. Pleasant fragrance to the flowers.
3. Freely branching with numerous flowering stems per plant.
4. Long stem length.
5. Excellent postproduction longevity.

The new rose plant has not been observed under all possible environmental conditions. The phenotype may vary significantly with variations in environment such as temperature, light or fertility level, without, however, any variance in genotype.

BRIEF DESCRIPTION OF PHOTOGRAPH

The accompanying colored photograph illustrates the new rose plant, showing the colors as true as it is reasonably possible to obtain in colored reproductions of this type. The photograph comprises a top perspective view of typical flowering stems of the new rose plant grown in Rijsenhout, The Netherlands. Flower and foliage color in these photographs may appear different from the actual colors due to light reflectance.

DETAILED BOTANICAL DESCRIPTION

The following observations, measurements, values, and comparisons describe plants grown in Rijsenhout, The Netherlands, under glass with average day temperatures of 19° C. and average night temperatures of 17° C.

In the following description, color references are made to The Royal Horticultural Society Colour Chart except where general terms of ordinary dictionary significance are used.

Classification:

*Botanical.*—*Rosa hybrida* cultivar Presur.

*Commercial.*—Cut rose.

Parentage:

*Male or pollen parent.*—*Rosa hybrida* proprietary selection P7.

*Female of seed parent.*—*Rosa hybrida* proprietary selection P24.

Propagation:

*Type.*—Cuttings.

*Time to initiate roots.*—About 12 days with soil temperatures of 25° C.

*Time to develop roots.*—About 25 days with soil temperatures of 25° C.

*Rooting habit.*—Fine, fibrous and well-branched.

Plant description:

*Form.*—Upright.

*Growth habit.*—Moderately vigorous. Freely branching and dense growth.

*Plant size.*—About 80 cm in height and about 40 cm in width.

*Productivity.*—About 360 stems per square meter per year under greenhouse year-round production.

*Stem and lateral branches.*—Quantity of lateral branches: Typically five. Length of lateral branches: About 75 cm. Internode length: About 7 cm. Color: 139B. Prickles: Present, moderate in number. Length: About 8 mm. Color: Apex: 34A. Base: 196A.

*Foliage description.*—Leaves arranged alternately, compound with three, five or seven leaflets per leaf, and generally symmetrical. Of the apical nine compound leaves, typically the distal leaf has three leaflets, the next leaf has five leaflets and the proximal seven leaves have seven leaflets. Quantity of leaves: About nine per lateral branch. Length, seven-leaflet leaf: About 18 cm. Width, seven-leaflet leaf: About 15 cm. Length of leaflet of seven-leaflet leaf: About 7.2 cm width of leaflet of seven-leaflet leaf: About 5 cm. Shape: Ovate with acute apex and obtuse base. Margin: Serrate. Texture: Smooth, somewhat glossy. Petiole length: About 3 cm. Petiole diameter: About 2 mm. Stipule: Foliaceous, aduate to petiole. Color: Young foliage, upper side: 147B. Young foliage, under side: 197B. Mature foliage, upper side: 131A. Mature foliage, under side: 147B. Venation, upper side: 131A. Venation, under side: 147B. Petiole: 131A.

Flower description:

*Flower type and habit.*—Large soft orange flowers that are golden yellow before opening. Consistently symmetrical rosette flowers. Freely and continuous flowering. Flowers borne singly at terminal apices or in clusters of up to four each. Flowers persistent.

*Flowering season.*—Year-round under greenhouse conditions.

*Rate of flower opening.*—About 10 days.

*Frangrance.*—Faint, pleasant, typical of Rosa.

*Flower diameter.*—About 11.5 cm.

*Flower depth (height).*—About 7 cm.

*Flower longevity on plant.*—About 22 days.

*Flower longevity as a cut flower.*—About 17 days.

*Flower buds.*—Shape: Ovate. Length: About 4.7 cm. Diameter: About 2.8 cm. Color: 15B.

*Petals/petaloids.*—Quantity: About 31 per flower. Typically about three rows with about 10 petals each. Length: About 5.5 cm. Width: About 6.3 cm. Shape: Rounded with mucronate apex. Aspect: Petals reflex as the flowers open. Margin: Undulate and entire. Texture: Satiny and rippled. Color: Upper side, when opening: 15B to 27C. Under side, when opening: 15C. Upper side, fully opened: 27C. Under side, fully opened: 158C. Fading to: 158C.

*Sepals.*—Quantity: Typically five per flower. Calyx length: About 2.8 cm. Calyx width: About 3.5 cm. Shape: Subulate with aristate tip. Color: Upper side: 137D. Under side: 138D.

*Peduncles.*—Strength: Very strong. Aspect: Erect. Length: About 6.5 cm. Texture: Smooth. Color: 137C.

*Reproductive organs.*—Stamens: Quantity: About 60 per flower. Stamen color: 45D. Anther size: Length, about 4 mm and width, about 1 mm. Anther shape: Ovate. Anther Color: 22A. Pollen: Moderate, 10C in color. Pistils: Quantity: About 85 per flower. Pistil length: About 1.2 cm. Style color: 155B/181A. Stigma color: 5C. Ovary color: 155B.

Seed description:

*Length.*—About 6 mm.

*Width.*—About 4 mm.

*Color.*—158D.

Disease resistance: Moderate resistance to Powdery Mildew has been observed under commerical greenhouse production conditions.

It is claimed:

1. A new and distinct rose plant named 'Presur', as illustrated and described.

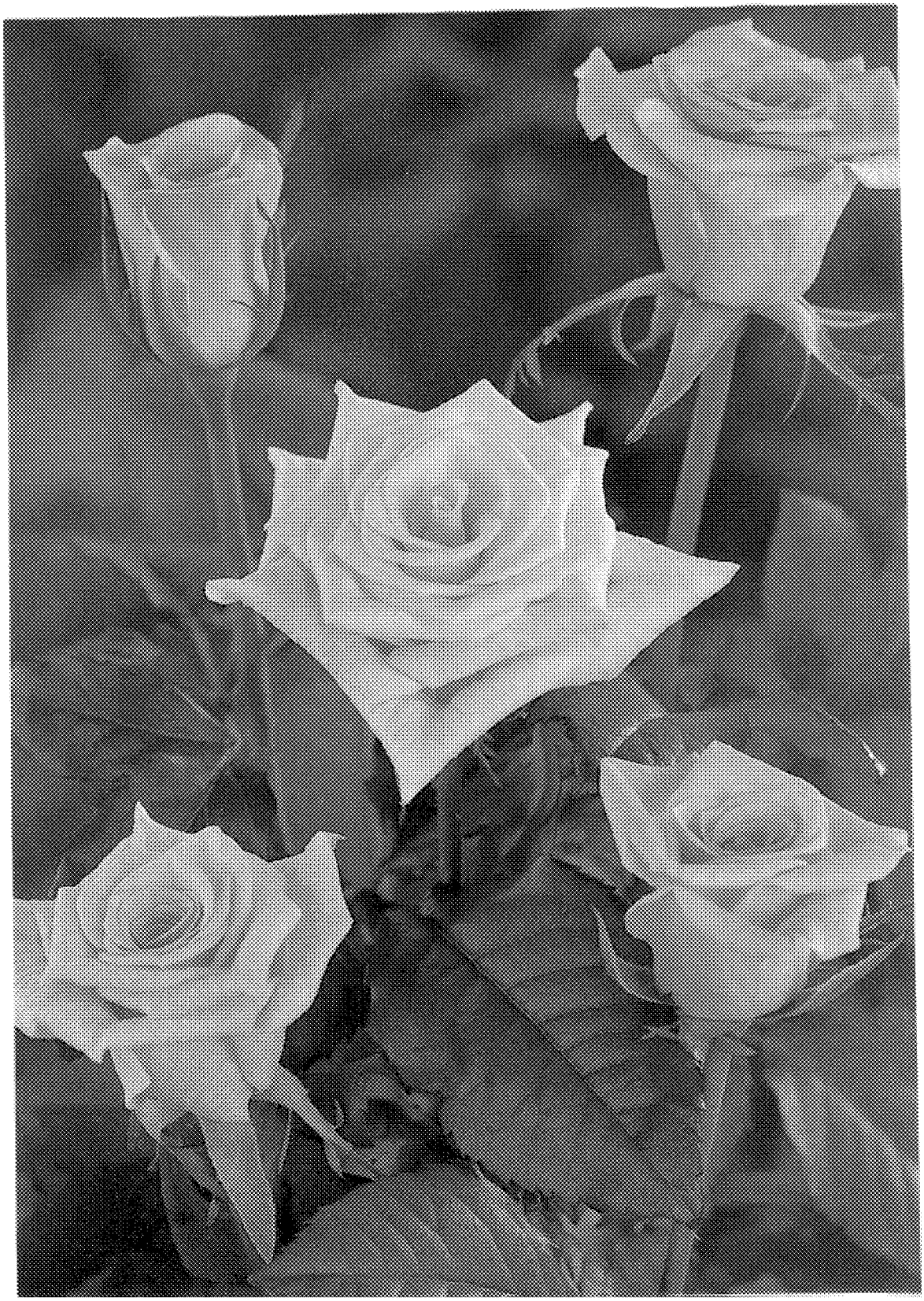

* * * * *